United States Patent
Inderbitzen et al.

(10) Patent No.: US 6,245,040 B1
(45) Date of Patent: Jun. 12, 2001

(54) PERFUSION BALLOON BRACE AND METHOD OF USE

(75) Inventors: Mark Inderbitzen, Miramar; Kirk Johnson, Miami Lakes; Susana Martinez, Pembroke Pines, all of FL (US)

(73) Assignee: Cordis Corporation, Miami, FL (US)

( * ) Notice: Subject to any disclaimer, the term of this patent is extended or adjusted under 35 U.S.C. 154(b) by 1105 days.

(21) Appl. No.: 08/705,005

(22) Filed: Aug. 29, 1996

Related U.S. Application Data

(63) Continuation of application No. 08/413,790, filed on Mar. 30, 1995, now abandoned, which is a continuation of application No. 08/182,768, filed on Jan. 14, 1994, now abandoned.

(51) Int. Cl.[7] .................................................. A61M 29/00
(52) U.S. Cl. ...................................... 604/103.07; 606/194
(58) Field of Search .................................. 602/192, 194, 602/159; 604/96, 103, 96.01, 103.07, 103.08; 606/195, 198

(56) References Cited

U.S. PATENT DOCUMENTS

| | | |
|---|---|---|
| 3,889,686 | 6/1975 | Duturbure . |
| 4,183,102 | 1/1980 | Guiset . |
| 4,233,983 | 11/1980 | Rocco . |
| 4,423,725 | 1/1984 | Baran et al. . |
| 4,447,227 | 5/1984 | Kotsanis . |
| 4,581,017 | 4/1986 | Sahota . |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 8/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,890,611 * | 1/1990 | Monfort et al. ................ 606/159 |
| 4,892,519 | 1/1990 | Songer et al. . |
| 4,909,252 | 3/1990 | Goldberger . |
| 4,983,167 | 1/1991 | Sahota . |
| 5,000,734 | 3/1991 | Boussignac et al. . |
| 5,000,743 | 3/1991 | Patel . |
| 5,006,119 | 4/1991 | Acker et al. . |
| 5,019,042 | 5/1991 | Sahota . |
| 5,035,694 | 7/1991 | Kasprzyk et al. . |
| 5,046,503 | 9/1991 | Schneiderman . |
| 5,078,685 | 1/1992 | Colliver . |
| 5,087,247 | 2/1992 | Horn et al. . |
| 5,090,958 | 2/1992 | Sahota . |

(List continued on next page.)

FOREIGN PATENT DOCUMENTS

WO9317748   9/1993   (WO) .

Primary Examiner—Michael H. Thaler
Assistant Examiner—William W. Lewis
(74) Attorney, Agent, or Firm—Cook, Alex, McFarron, Manzo, Cummings & Mehler Ltd.

(57) ABSTRACT

A dilation catheter suitable for use in medical procedures is provided which includes a balloon disposed on an elongated flexible tube. The tube is capable of passing fluid between the balloon and the tube for varying the balloon between a collapsed and expanded condition. The catheter includes a brace fitted over the balloon for restricting expansion of a selected portion of the balloon for forming a perfusion channel that allows fluid to be perfused past the balloon when it is expanded in a body vessel. A medical procedure for dilation under perfusion conditions is also provided.

28 Claims, 2 Drawing Sheets

U.S. PATENT DOCUMENTS

| | | |
|---|---|---|
| 5,090,960 | 2/1992 | Don Michael . |
| 5,108,370 | 4/1992 | Walinsky . |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |
| 5,181,911 | 1/1993 | Shturman . |
| 5,195,955 | 3/1993 | Don Michael . |
| 5,195,971 | 3/1993 | Sirhan . |
| 5,209,749 * | 5/1993 | Buelna ................. 606/159 |
| 5,222,941 | 6/1993 | Don Michael . |
| 5,226,888 | 7/1993 | Arney . |
| 5,232,446 | 8/1993 | Arney . |
| 5,257,974 * | 11/1993 | Cox ..................... 606/194 |
| 5,261,879 | 11/1993 | Brill . |
| 5,295,959 * | 3/1994 | Gurbel et al. ........... 606/194 |
| 5,295,995 * | 3/1994 | Kleiman ................. 606/194 |

* cited by examiner

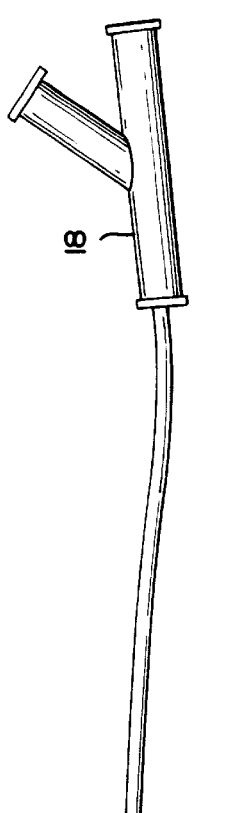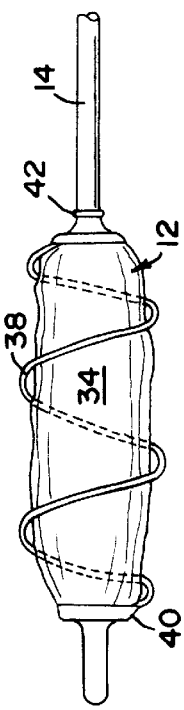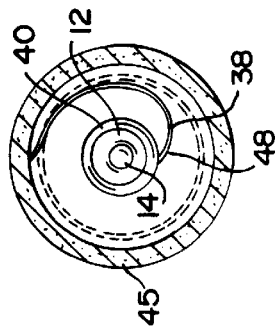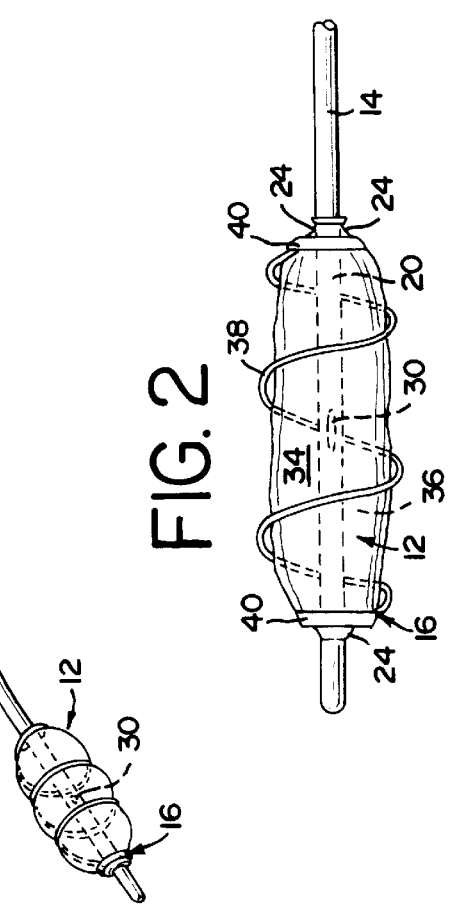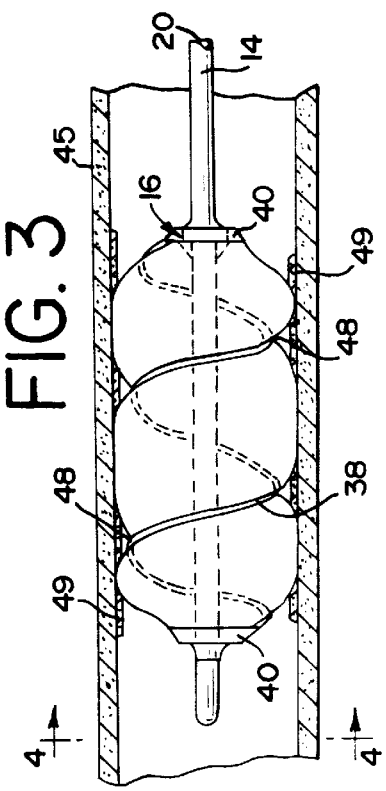

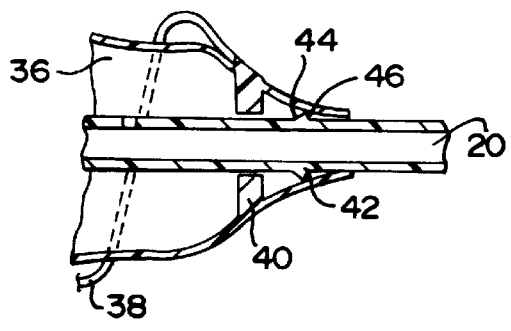
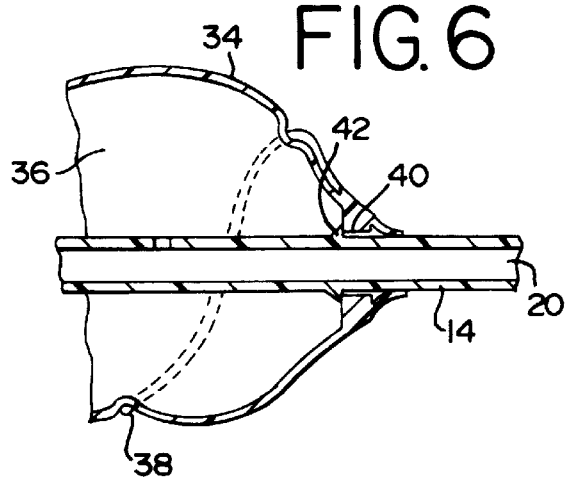
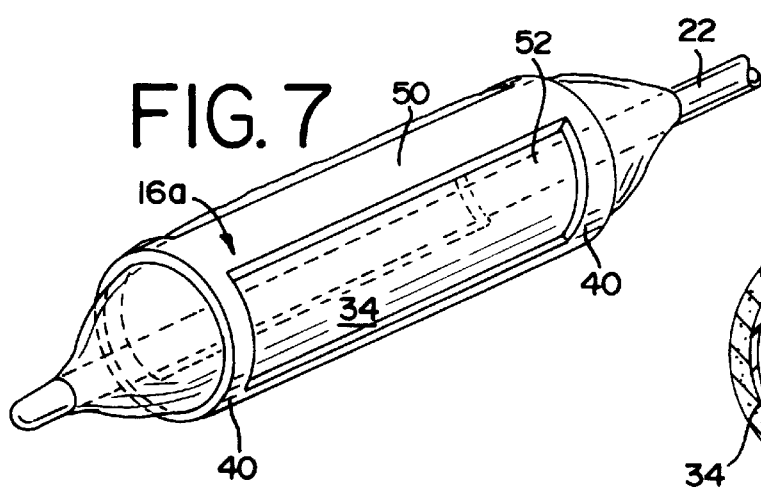
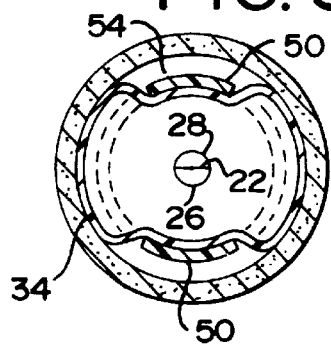
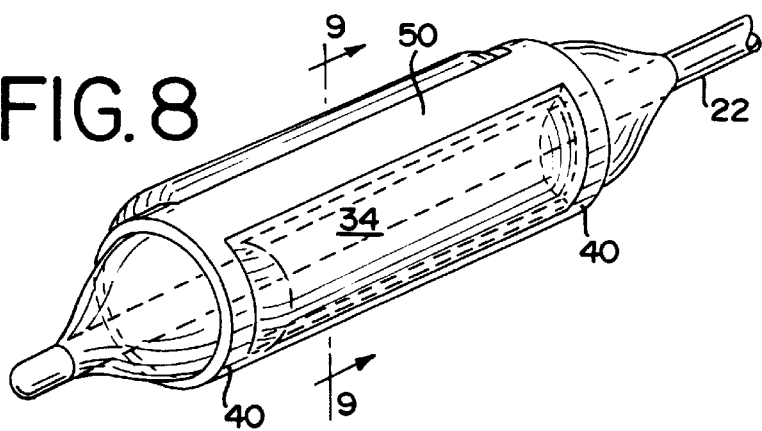

PERFUSION BALLOON BRACE AND METHOD OF USE

This application is a continuation of Ser. No. 08/413,790 filed Mar. 30, 1995 abandoned which is a continuation of Ser. No. 08/182,768 filed Jan. 14, 1994 abandoned.

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon as well as a method for converting standard dilation balloons to perfusion balloons.

BACKGROUND AND SUMMARY OF THE INVENTION

PTCA procedures generally include inflation of a balloon in an arterial passage in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wijay, et al., U.S. Pat. No. 5,158,540, discloses a perfusion catheter that perfuses blood during the balloon's inflation cycle to allow for longer inflation periods; however, the catheter is extremely complicated structurally and expensive to manufacture.

It is, therefore a general object of the present invention, to provide a brace to impart perfusion attributes to a balloon dilation catheter suitable for PTCA procedures.

Another object of the invention is to provide a modified dilation catheter and procedure of its use for PTCA procedures wherein blood perfuses around the inflated balloon and permits prolonged inflation times for the balloon.

Another object of the present invention is to provide a perfusion brace for a dilation catheter and which is of a relatively simple structure for use in PTCA procedures where blood is perfused distally of the inflated balloon.

Another object of the present invention is to provide a brace for easily converting a standard non-perfusion dilation balloon into a balloon that perfuses blood past the balloon when the balloon is inflated in the artery.

The present invention overcomes the problems associated with the prior art perfusion catheters by providing a perfusion brace on a balloon catheter with a balloon that may be varied between a collapsed condition of a size allowing the catheter to be transported through a body vessel and an expanded condition of a size allowing the exterior surface of the balloon to engage a body vessel wall. The perfusion brace is fixed around the balloon and restricts radial expansion of a portion of the balloon that traverses the length of the balloon while at the same time allowing the remaining portion of the balloon to extend to its full expanded condition. A channel for perfusing fluid past the expanded balloon is thereby formed along the restriction defined by the brace, the channel being further defined by the expanded portions of the balloon.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

BRIEF DESCRIPTION OF THE DRAWINGS

FIG. 1 is a perspective view of a perfusion balloon catheter made according to the present invention;

FIG. 2 is an enlarged elevational view of a portion of the catheter of FIG. 1 shown in its collapsed condition;

FIG. 2A is an elevational view of a perfusion balloon catheter made according to the present invention illustrating a balloon that is integrally formed with the flexible tubular shaft;

FIG. 3 is an elevational view of the catheter of FIG. 2, shown in its expanded condition and disposed within a body vessel, illustrated in cross-section;

FIG. 4 is an end view of the catheter of FIG. 3 taken along line 4—4;

FIG. 5 is a cross-sectional view, partially broken away, of the catheter of FIG. 3 taken along line 5—5 illustrating a brace locking mechanism;

FIG. 6 is a cross-sectional view, partially broken away, of the catheter of FIG. 3 illustrating the brace in the locked position in engagement with the brace locking mechanism;

FIG. 7 is a perspective view of an alternate embodiment of a portion of a perfusion balloon catheter made according to the present invention illustrating the balloon in its collapsed condition;

FIG. 8 is a perspective view of the embodiment of FIG. 7 illustrating the balloon in its expanded condition; and, FIG. 9 is a cross-sectional view of the balloon of FIG. 8 taken along line 9—9 and disposed in a body vessel.

DETAILED DESCRIPTION OF THE PREFERRED EMBODIMENT

While the invention may be embodied in a variety of forms and used in different applications such as angioplasty, valvuloplasty, and urological uses, a description of particular embodiments of the inventive concept will be made in the form of dilation catheters for use in PTCA procedures. As illustrated in the drawings, the perfusion balloon catheter, generally designated at 10 in FIG. 1, made according to the present invention comprises an extensible balloon 12 located substantially near the distal end of an elongated flexible tubular shaft 14 and a brace member 16. The illustrated catheter includes a hub 18, of a type well known in the art. Any suitable fitting and/or hub can be provided as desired.

As shown in FIGS. 3, 5, and 6, a lumen 20 is formed in tubular shaft 14 and may be of a substantially small diameter similar to that of the outer diameter of a standard guidewire, preferably having a diameter of between about 0.008 inch and about 0.020 inch. Lumen 20 is utilized for carrying fluid, such as radiopaque saline solution or other fluid of a type well known in the art. The fluid carried by lumen 20 is communicated to balloon 12 for inflating and deflating balloon 12. It should be understood that the diameter of lumen 20 is large enough to carry sufficient amounts of fluid for inflating balloon 12 sufficiently quickly.

An alternate embodiment of the flexible tubular shaft 22 is shown in FIG. 9 and illustrates a dual lumen catheter, including lumen 26 and lumen 28. As illustrated, lumen 26 is substantially larger in cross-sectional area than lumen 28 and may be utilized to carry fluid to and from balloon 12 similarly to that of lumen 20. Lumen 28 may be utilized to receive a guidewire to provide assistance in placing the dilation catheter at the appropriate position in a body vessel. The present invention can be used with a fixed-wire, over-the-wire, or rapid exchange PTCA system.

Flexible tubing 14 utilized in the present invention is preferably formed of a suitable thermoplastic material, such as polyethylene, polyvinylchloride, nylon, polyurethane, polyamide and the like, or from a composite structure. Fluid is communicated to the interior of the balloon through opening 30 shown in FIGS. 1 and 2. It is preferred that the opening 30 be a slit that extends longitudinally with the flexible tube to prevent propagation of the openings while the tube 14 is being manipulated during insertion into a body vessel. Other shapes of openings and connections, such as circular openings, may also be utilized to pass fluid between the tubing shaft 14 and the interior of the balloon 12. Although one opening is illustrated between the flexible tube 14 and balloon 12, any number of openings may be utilized to pass fluid between the flexible tube and the interior of the balloon 12.

Alternatively, the balloon 12 may be formed integrally with the flexible tubular shaft as illustrated in FIG. 2A in a manner well known in the art and described, for example, in Pinchuk, et al., U.S. Pat. No. 5,156,612. In this embodiment, no opening 30 is required as the fluid would directly flow out of tubular shaft and into the balloon to expand it as the fluid is pumped through tubular shaft 14.

The balloon 12 is generally cylindrically shaped and includes an inner surface 32 and an exterior surface 34. The balloon is in seal providing communication about its respective edges 24 to the flexible tube or integrally formed therewith as described above, defining an interior compartment 36. The balloon may be inflated to an expanded condition by the introduction of fluid into interior compartment 36. When fluid is removed from interior compartment 36 the balloon returns to a collapsed condition.

Catheter 10 also includes a brace 16 as illustrated in FIG. 2. The brace includes a pair of end rings 40 spaced apart and disposed at the approximate proximal and distal ends of the balloon. The rings 40 are connected by a spiral member 38 that wraps around the balloon and is substantially coaxial with the tubular shaft and the balloon, extending for approximately the entire length of the balloon. The brace may be made of a metal such as stainless steel or of a suitable plastic material. The helically shaped brace may also be made of a suture material or other strong thread tied at the ends of the balloon and wrapped around the balloon between the ties.

Brace 16 may be connected to the catheter by sliding it onto the distal end of the catheter and positioning it in overlying relationship with the balloon. The rings 40 fit snugly around the respective distal and proximal ends of the balloon which overly the flexible tubular shaft holding the brace in position. The fit should not be so tight as to pinch the tube 14 and prevent fluid flow through the tubular shaft 14. To insure that the brace remains attached to the tubular shaft, the shaft may include a barb 42, which may be annular or may be positioned on only a portion of the circumference of the shaft.

FIG. 5 illustrates the proximal end ring 40 as it is being slid in a proximal direction toward the barb. The barb has an angled surface 44 and a surface 46 extending substantially normal to the tubular shaft 14. When the brace is slid on the catheter from the position illustrated in FIG. 5 to that illustrated in FIG. 6, the interior portion of the ring will ride up angled surface 44 of the barb and then drop into position in engagement with surface 46. It should be understood that the barb may be positioned on either the distal or proximal end of the balloon for engagement with either or both of the rings. It is preferred that surface 46 be positioned proximally of the angled surface 44 with respect to the catheter to minimize the possibility that the brace will slip off of the balloon when the catheter is removed from a body vessel and as the catheter is pulled longitudinally in the proximal direction with respect to the body vessel.

Alternatively, the brace can be secured onto the catheter in a more permanent manner, such as by heat welding, adhesives, shrink tubing or molding. In that instance no barb or other sliding securement device need be included.

As illustrated in FIG. 2, the balloon 12 is shown in a substantially collapsed condition and the exterior surface 34 of the balloon is not substantially constrained by the spiral member 38 of the brace, typically being spaced radially inwardly at least along portions of the brace. The outer diameter of the brace should be of a size permitting the catheter to be easily transported through an appropriate body vessel without significantly causing trauma to the body vessel wall or preventing the flow of fluid through the body vessel.

The balloon 12 may be varied between the collapsed condition as illustrated in FIG. 2 and the expanded condition as illustrated in FIG. 3. In its expanded condition, the exterior surface 34 of the balloon extends radially away from the tubular shaft 14 for engaging and dilating the body vessel wall 45 and a stenosis 49 or the like thereon. When the balloon is expanded, the brace 46 prevents a portion of the balloon from extending radially away from the shaft. This forms a spiral channel 48 that extends across the exterior surface of the balloon and traverses a path that runs substantially the entire length or longitudinal extent of the balloon. The channel 48 is spaced radially inwardly from the extended exterior surface. When the balloon is expanded in a body vessel, the spiral channel 48 permits fluid to flow past the inflated balloon without the need for extrinsic pumping or routing mechanisms.

One advantage associated with the spiral geometry of the balloon of this embodiment of the present invention is that the balloon has a substantially circular profile at any given point along its length. This profile eliminates the need to know the orientation of the balloon in the vessel or the effects of a non-circular geometry on possible vessel trauma.

Another advantage of the spiral geometry is that there is no need to rotate the balloon in the vessel to insure that the entire surface of the lesion or defect is dilated as is required in balloons having non-circular profiles. Precisely rotating the balloon catheters may be quite difficult due to the length of the flexible tube utilized. On the other hand, this embodiment of the present invention need only be advanced or retracted to a small extent in the longitudinal direction within the body vessel to effectively dilate the entire surface of the stenosis, including its areas opposite the spiral channel 48 during initial inflation.

It will be appreciated that braces in accordance with the present invention, when of the slide-on type, may be utilized with a standard balloon catheter to convert the standard dilation balloon catheter into a perfusion catheter.

Balloon 12 is to be produced from material that exhibits compliance adequate to expand as discussed herein. Examples include polyethylene, latex rubber, polyvinyl chloride, nylon, polyamide, polyethylene terephthalate (PET), polyurethane or other suitable flexible, and somewhat elastic material. Preferably, the material will be at least as compliant as nylons such as Nylon 12.

In a typical procedure according to the invention, a balloon catheter may be outfitted with a brace made according to the present invention by sliding the brace 16 over the distal end of the catheter into a position overlying the balloon and properly engaged to the annular barb 42, when provided. Whether the brace is thus slid in place or more permanently secured, the catheter is then generally advanced as desired, such as from the femoral artery or the Tee-brachial artery up the aortic root and positioned in the appropriate coronary artery. Advancement of the catheter through an artery or body vessel is performed when the balloon is in its collapsed, non-inflated condition. The balloon, which is disposed at or near the distal end of the catheter, is positioned across a restriction or stenosis in the artery. Thereafter, the balloon is inflated in the artery by pumping fluid through the lumen of the flexible tubing. Inflation of the balloon extends the balloon radially outwardly causing the exterior surface to engage the stenosis or vessel wall and dilate the vessel wall. The brace, particularly its associated spiral member, prevents radial extension of a portion of the balloon, forming the longitudinally extending spiral channel. The spiral channel is spaced radially inwardly from the exterior surface engaging the body vessel wall allowing the blood to be perfused past the expanded balloon. This allows the balloon to remain expanded in the artery for a considerably longer period of time than conventional catheters as explained above. When deemed necessary, the balloon may then be deflated and advanced or retracted longitudinally to a small extent and then reinflated to ensure that the entire surface of the stenosis has been effectively dilated.

When utilizing the perfusion brace catheter made according to the present invention, a guidewire typically is first inserted into the body vessel. This can be facilitated when the catheter is of the dual lumen type or any over-the-wire or rapid exchange catheter system discussed herein. The catheter may then be inserted over the guidewire wherein the guidewire extends through a lumen to assist in positioning the catheter in the body vessel. After the perfusion catheter has performed its function of dilating the restricted artery or the tube, the balloon may be deflated and the catheter removed.

An alternative embodiment of the perfusion brace catheter made according to the present invention is illustrated in FIGS. 7–9. In this embodiment a dilation balloon catheter including a tubular shaft and balloon are utilized as discussed herein, the main difference being the construction of the brace. Like reference numerals will therefore be utilized to identify corresponding parts.

Brace 16a of this embodiment includes two spaced end rings 40 which are generally coaxial with each other. End rings 40 are connected by at least one longitudinally extending strut 50. Any number of struts 50 may be utilized, it is preferred however, that two circumferentially spaced longitudinally extending struts 50 be utilized with circumferentially extending openings or windows 52 being defined between the struts. As shown in FIG. 7, when balloon 12 is in its collapsed condition, its exterior surface is substantially flush with and/or generally spaced radially inwardly from the rings and the struts.

As illustrated in FIGS. 8 and 9, when the balloon is in its expanded position, portions of the exterior surface 34 of the balloon 12 extend radially outwardly through the windows 52. The struts prevent radial expansion of longitudinally extending portions of balloon 12 located thereunder, forming longitudinally extending channels 54 (FIG. 9) that are spaced radially inwardly from the exterior surface of the balloon. Thus, when the catheter is disposed in a body vessel as in FIG. 9, the exterior surface of the balloon in its expanded condition is capable of engaging the body vessel wall and dilating the body vessel wall. Simultaneously, channels 54 spaced radially inwardly from the exterior surface of the balloon and of the vessel wall are formed and extend longitudinally the length of the balloon, providing a passageway for fluid to be perfused past the expanded balloon. The brace 16a is connected to the catheter in the same manner as described above or by any suitable connection means. It can be generally permanently secured, or it can be secured by sliding action. In the latter event, at least one of the rings 40 can slidingly engage an annular barb 42 disposed on the tubular shaft 22.

One advantage of the present invention is its low profile which allows the catheter to be easily positioned in an appropriate body vessel and provide sufficient blood flow past the balloon.

Another advantage of the present invention is that the use of the brace allows a single standard balloon catheter to be used as a perfusion catheter or simply a standard catheter depending on the treatment desired by the physician.

Procedures carried out with this alternate embodiment of the present invention are substantially the same as previously described except that in order to insure that the entire surface of the stenosis is dilated, the balloon may be deflated and rotated in the body vessel and then reinflated.

It will thus be seen that the present invention provides a new and useful perfusion catheter having a number of advantages and characteristics, including those pointed out herein and others which are inherent in the invention. Preferred embodiments of the invention have been described by way of example, and it is anticipated that modifications may be made to the described forms without departing from the spirit of the invention or the scope of the appended claims.

We claim:

1. A perfusion dilation catheter for use in medical procedures comprising:

an elongated tubular shaft; a dilation balloon disposed on said tubular shaft, said balloon having opposite ends and exterior surface; means for passing fluid between said tubular shaft and said balloon to vary said balloon between a collapsed condition of a size allowing said catheter to be transported through a body vessel and an expanded condition of a size allowing said exterior surface to engage a body vessel wall;

a profusion brace disposed about said balloon independently of and in substantially non-compressive relationship to the exterior surface of said balloon when said balloon is in its collapsed condition, said perfusion brace being positioned to engage and restrict the expansion of a selected portion of said balloon when said balloon is radially expanded while permitting radial expansion of the remaining portion of said balloon to an extent greater than the expansion of the selected portion to define a perfusion channel spaced radially outwardly from said selected portion of the balloon when said balloon is in its expanded condition, spaced radially inwardly from said remaining portion of the balloon in its expanded condition, and communicating between said opposite ends of said balloon; and both of said selected portion and said remaining portion of the exterior surface of the balloon are radially spaced from said tubular shaft when said balloon is in its expanded condition.

2. The perfusion catheter of claim 1, wherein said remaining portion of the exterior surface, when said balloon is in its collapsed condition, has a radial extent which is substantially no greater than the radial extent of said brace.

3. The perfusion catheter of claim 1, wherein said remaining portion of the exterior surface is spaced radially outwardly from said brace when said balloon is in its expanded condition.

4. The perfusion catheter of claim 1, wherein said brace includes a pair of spaced rings connected by a helical member that extends substantially the entire length of the balloon.

5. The perfusion catheter of claim 1, wherein said means for passing fluid includes at least one pathway between said tubular shaft and said balloon.

6. The perfusion catheter of claim 1, wherein said balloon is integrally formed with said tubular shaft.

7. The perfusion catheter of claim 1, wherein said brace includes a pair of spaced rings connected by at least one longitudinally extending strut.

8. The perfusion catheter of claim 1, wherein said balloon is constructed of a relatively compliant material.

9. The perfusion catheter of claim 1, wherein said perfusion brace is radially spaced from said tubular shaft when said balloon is in its collapsed condition.

10. A perfusion brace for transforming a dilation balloon catheter into a perfusion balloon catheter, said perfusion brace comprising:

at least two spaced apart rings, said rings being substantially coaxial with each other and connected by at least one perfusion channel defining member to define a perfusion brace that is slidable onto a collapsed dilation balloon of a catheter to transform the catheter into a perfusion balloon catheter;

said perfusion channel defining member being independent of and dimensioned to be in substantially non-compressive relationship to the exterior surface of the balloon when positioned on the collapsed balloon, but restricting radial expansion of a selected portion of the dilation balloon when the balloon is radially expanded with the brace thereon, said perfusion channel defining member also being dimensioned to extend over substantially the length of the dilation balloon and having a radial extent which is less than the radial extent of the dilation balloon when expanded in order to define a perfusion channel on the balloon radially outwardly of said perfusion channel defining member when said perfusion brace is positioned on the dilation balloon and the dilation balloon is expanded.

11. The perfusion brace of claim 10, further including means for preventing longitudinal movement of said brace with respect to said balloon catheter after the perfusion brace has been slid onto the dilation balloon.

12. The perfusion brace of claim 11, wherein said means for preventing longitudinal movement includes a flange extending from one of said annular rings for cooperating with a portion of said catheter.

13. The perfusion brace of claim 10, wherein said perfusion channel defining member is helically shaped.

14. The perfusion brace of claim 10, wherein said perfusion channel defining member includes at least one longitudinally extending strut.

15. An improved perfusion balloon catheter of a type having an elongated flexible tubular shaft, an extensible balloon disposed on said shaft, said balloon having opposite ends and an exterior surface and being inflatable between a collapsed condition of a size allowing transport through a body vessel and an expanded condition of a size allowing said exterior surface to engage a body vessel wall, and means for passing fluid between said tubular shaft and said balloon for varying said balloon between said collapsed and expanded conditions, the improvement comprising: a brace disposed about said balloon independently of and in substantially non-compressive relationship to the exterior surface of said balloon when said balloon is in its collapsed condition; said brace being positioned to engage and restrict expansion of a selected portion of said balloon when said balloon is radially expanded while permitting radial expansion of the remaining portion of said balloon to an extent greater than the expansion of the selected portion to define a perfusion channel when said balloon is in its expanded condition, spaced radially inwardly from said remaining portion of the balloon in its expanded condition, and communicating between said opposite ends of said balloon; and both of said selected portion and said remaining portion of the exterior surface of the balloon are radially spaced from said tubular shaft when said balloon is in its expanded condition.

16. The improved perfusion balloon catheter of claim 15, wherein said brace includes at least two spaced coaxial rings, said rings connected by at least one perfusion channel defining member that extends substantially the entire length of the expanded balloon in its expanded condition.

17. The improved perfusion balloon catheter of claim 16, wherein said perfusion channel defining member is substantially helically shaped.

18. The improved perfusion balloon catheter of claim 16, wherein said perfusion channel defining member is at least one longitudinally extending strut.

19. The improved perfusion balloon catheter of claim 15, further including means for preventing longitudinal movement of said brace in a first direction.

20. The improved perfusion balloon catheter of claim 19, wherein said means for preventing longitudinal movement includes a barb disposed on said tubular shaft for cooperating with a portion of said brace.

21. The improved perfusion balloon catheter of claim 15, wherein said balloon is constructed of a relatively compliant material.

22. The improved perfusion balloon catheter of claim 15, wherein said brace is radially spaced from said tubular shaft when said balloon is in its collapsed condition.

23. A method of performing percutaneous transluminal coronary angioplasty comprising the steps of:

providing an elongated tubular catheter shaft and a dilation balloon disposed on said shaft, said balloon having an exterior surface and being inflatable between a collapsed condition and an expanded condition;

placing a perfusion brace over the exterior surface of said balloon and said shaft when said balloon is in its collapsed condition, said perfusion brace being independent of and in substantially non-compressive relationship to the exterior surface of said balloon when said balloon is in its collapsed condition;

inserting said catheter into a body vessel and aligning said balloon adjacent an area of said body vessel upon which the angioplasty is to be performed;

inflating said balloon to its expanded condition in which a dilating portion of said exterior surface of the balloon engages said area of said body vessel while simultaneously restricting expansion of a selected portion of said exterior surface of the balloon by engaging the perfusion brace to form a perfusion channel spaced radially inwardly from said dilating portion of the exterior surface of the balloon; and perfusing body fluid past said balloon through the perfusion channel.

24. The method of claim 23, further including the step of deflating said balloon from its expanded condition to its collapsed condition and repositioning and reinflating said balloon in said body vessel to insure that the entire said area of the body vessel is engaged by said balloon in its expanded condition.

25. The method of claim 24, wherein said repositioning step includes moving the balloon in a longitudinal direction until the dilating portion of the balloon moves to a location along the vessel area that had been opposite to said selected portion of the balloon during said inflating step.

26. The method of claim 24, wherein said repositioning step includes rotating the balloon until the dilating portion of the balloon moves to a location along the vessel area that had been opposite to said selected portion of the balloon during said inflating step.

27. The method of claim 23, wherein said perfusion brace is radially spaced from said tubular shaft when said balloon is in its collapsed condition.

28. The method of claim 23, wherein both of said selected portion and said dilating portion of the exterior surface of the balloon are radially spaced from said tubular catheter shaft when said balloon is in its expanded condition.

\* \* \* \* \*